(12) United States Patent
Wilson

(10) Patent No.: US 9,526,290 B2
(45) Date of Patent: Dec. 27, 2016

(54) ADHESIVE MOUNTABLE STACK OF REMOVABLE LAYERS

(71) Applicant: Racing Optics, Inc., Las Vegas, NV (US)

(72) Inventor: Bart E. Wilson, Las Vegas, NV (US)

(73) Assignee: Racing Optics, Inc., Las Vegas, NV (US)

( * ) Notice: Subject to any disclaimer, the term of this patent is extended or adjusted under 35 U.S.C. 154(b) by 0 days.

(21) Appl. No.: 15/050,293

(22) Filed: Feb. 22, 2016

(65) Prior Publication Data

US 2016/0242963 A1    Aug. 25, 2016

Related U.S. Application Data

(62) Division of application No. 14/307,189, filed on Jun. 17, 2014, now Pat. No. 9,295,297.

(51) Int. Cl.
*A42B 3/26*    (2006.01)
*A61F 9/02*    (2006.01)

(52) U.S. Cl.
CPC ........ *A42B 3/26* (2013.01); *A61F 9/025* (2013.01)

(58) Field of Classification Search
CPC .............. A42B 3/26; A42B 3/226; A42B 3/20
See application file for complete search history.

(56) References Cited

U.S. PATENT DOCUMENTS

| 2,511,329 | A |   | 6/1950 | Craig |
| 3,785,102 | A |   | 1/1974 | Amos |
| 3,948,662 | A |   | 4/1976 | Alston et al. |
| 3,950,580 | A |   | 4/1976 | Boudet |
| 4,076,373 | A |   | 2/1978 | Moretti |
| 4,090,464 | A |   | 5/1978 | Bishopp et al. |
| 4,138,746 | A | * | 2/1979 | Bergmann ............... A42B 3/26 2/10 |
| 4,204,231 | A |   | 5/1980 | Permenter |

(Continued)

FOREIGN PATENT DOCUMENTS

| DE | 3637188 | 5/1988 |
| DE | 19808535 | 9/1999 |

(Continued)

OTHER PUBLICATIONS

Dupont Teijin Films, "Mylar Polyester Film—Optical Properties", Jun. 2003, 2 pages.

(Continued)

*Primary Examiner* — Shaun R Hurley
*Assistant Examiner* — Andrew W Sutton
(74) *Attorney, Agent, or Firm* — Stetina Brunda Garred & Brucker

(57) ABSTRACT

An eye protector includes a lens configured to protect the wearer from projectiles, and an optically clear stack attached to the lens. The stack can have one or more removable layers. The eye protector also includes an optically clear dry mount adhesive layer attaching the stack to the lens. The dry mount adhesive may be self-wetting to attach the stack to the lens so that air between the stack and the lens can be removed after the stack is attached and/or adhered to the lens, for example, by applying pressure across the surface of the stack. The refractive indices of the lens, the dry mount adhesive, and each removable layer are matched to within about 0.2.

5 Claims, 6 Drawing Sheets

(56) References Cited

U.S. PATENT DOCUMENTS

| | | | |
|---|---|---|---|
| 4,301,193 A | 11/1981 | Zuk | |
| 4,332,861 A | 6/1982 | Franz et al. | |
| 4,380,563 A | 4/1983 | Ayotte | |
| 4,696,860 A | 9/1987 | Epperson | |
| 4,716,601 A * | 1/1988 | McNeal | A61F 9/025 |
| | | | 2/434 |
| 4,842,919 A | 6/1989 | David et al. | |
| 4,889,754 A | 12/1989 | Vargas | |
| 4,907,090 A | 3/1990 | Ananian | |
| 4,934,792 A | 6/1990 | Tovi | |
| 5,002,326 A | 3/1991 | Westfield et al. | |
| H0001023 H | 3/1992 | Wiseman | |
| 5,104,929 A | 4/1992 | Bilkadi | |
| 5,194,293 A | 3/1993 | Foster | |
| 5,420,649 A | 5/1995 | Lewis | |
| 5,443,877 A | 8/1995 | Kramer et al. | |
| 5,471,036 A | 11/1995 | Sperbeck | |
| 5,486,883 A | 1/1996 | Candido | |
| 5,512,116 A | 4/1996 | Campfield | |
| RE35,318 E | 8/1996 | Warman | |
| 5,592,698 A * | 1/1997 | Woods | A42B 3/26 |
| | | | 2/424 |
| 5,633,049 A | 5/1997 | Bilkadi et al. | |
| 5,668,612 A | 9/1997 | Hung | |
| 5,671,483 A * | 9/1997 | Reuber | A42B 3/24 |
| | | | 2/424 |
| 5,694,650 A | 12/1997 | Hong | |
| 5,740,560 A | 4/1998 | Muoio | |
| 5,896,991 A | 4/1999 | Hippely et al. | |
| 5,972,453 A | 10/1999 | Akiwa et al. | |
| 5,991,072 A | 11/1999 | Solyntjes et al. | |
| 6,008,299 A | 12/1999 | McGrath et al. | |
| 6,085,358 A * | 7/2000 | Cogan | A42B 3/26 |
| | | | 2/424 |
| 6,250,765 B1 | 6/2001 | Murakami | |
| 6,305,073 B1 | 10/2001 | Badders, Jr. | |
| 6,388,813 B1 * | 5/2002 | Wilson | A42B 3/26 |
| | | | 359/630 |
| 6,461,709 B1 | 10/2002 | Janssen et al. | |
| 6,469,752 B1 | 10/2002 | Ishikawa et al. | |
| 6,536,045 B1 | 3/2003 | Wilson et al. | |
| 6,536,589 B2 | 3/2003 | Chang | |
| 6,555,235 B1 | 4/2003 | Aufderheide et al. | |
| 6,559,902 B1 | 5/2003 | Kusuda et al. | |
| 6,592,950 B1 | 7/2003 | Toshima et al. | |
| 6,660,389 B2 | 12/2003 | Liu et al. | |
| 6,750,922 B1 | 6/2004 | Benning | |
| 6,777,055 B2 | 8/2004 | Janssen et al. | |
| 6,800,378 B2 | 10/2004 | Hawa et al. | |
| 6,841,190 B2 | 1/2005 | Liu et al. | |
| 6,847,492 B2 * | 1/2005 | Wilson | A42B 3/26 |
| | | | 2/15 |
| 6,864,882 B2 | 3/2005 | Newton | |
| 6,870,686 B2 * | 3/2005 | Wilson | A42B 3/26 |
| | | | 359/642 |
| 6,879,319 B2 | 4/2005 | Cok | |
| 6,995,902 B2 | 2/2006 | Richardson | |
| 7,070,837 B2 | 7/2006 | Ross | |
| 7,184,217 B2 | 2/2007 | Wilson et al. | |
| 7,226,176 B1 | 6/2007 | Huang | |
| 7,351,470 B2 | 4/2008 | Draheim et al. | |
| 7,495,895 B2 | 2/2009 | Carnevali | |
| 7,629,052 B2 | 12/2009 | Brumwell | |
| 8,044,942 B1 | 10/2011 | Leonhard et al. | |
| 8,261,375 B1 | 9/2012 | Reaux | |
| 8,693,102 B2 | 4/2014 | Wilson et al. | |
| 9,295,297 B2 * | 3/2016 | Wilson | A42B 3/26 |
| 2001/0035936 A1 | 11/2001 | Maisnik | |
| 2002/0101411 A1 | 8/2002 | Chang | |
| 2002/0109922 A1 | 8/2002 | Wilson et al. | |
| 2002/0122925 A1 | 9/2002 | Liu et al. | |
| 2002/0159159 A1 * | 10/2002 | Wilson | A42B 3/26 |
| | | | 359/630 |
| 2002/0195910 A1 | 12/2002 | Hus et al. | |
| 2003/0012936 A1 | 1/2003 | Draheim et al. | |
| 2003/0087054 A1 | 5/2003 | Janssen et al. | |
| 2003/0110613 A1 | 6/2003 | Ross | |
| 2004/0004605 A1 | 1/2004 | David | |
| 2004/0109096 A1 | 6/2004 | Anderson et al. | |
| 2004/0121105 A1 | 6/2004 | Janssen et al. | |
| 2004/0202812 A1 | 10/2004 | Congard et al. | |
| 2004/0227722 A1 | 11/2004 | Friberg et al. | |
| 2005/0002108 A1 | 1/2005 | Wilson et al. | |
| 2006/0114245 A1 | 6/2006 | Masters et al. | |
| 2006/0285218 A1 | 12/2006 | Wilson et al. | |
| 2007/0019300 A1 | 1/2007 | Wilson et al. | |
| 2007/0181456 A1 | 8/2007 | Kusuda et al. | |
| 2007/0211002 A1 | 9/2007 | Zehner et al. | |
| 2007/0229962 A1 | 10/2007 | Mason, Jr. | |
| 2008/0030631 A1 | 2/2008 | Gallagher | |
| 2008/0055258 A1 | 3/2008 | Sauers | |
| 2008/0151177 A1 * | 6/2008 | Wang | G02C 7/12 |
| | | | 351/49 |
| 2009/0054115 A1 | 2/2009 | Horrdin et al. | |
| 2009/0086415 A1 | 4/2009 | Chipping | |
| 2009/0087655 A1 | 4/2009 | Yamada et al. | |
| 2009/0105437 A1 | 4/2009 | Determan et al. | |
| 2010/0026646 A1 | 2/2010 | Xiao et al. | |
| 2010/0102197 A1 | 4/2010 | McIntyre | |
| 2010/0238119 A1 | 9/2010 | Dubrovsky et al. | |
| 2010/0245273 A1 | 9/2010 | Hwang et al. | |
| 2010/0270189 A1 | 10/2010 | Pedersen, II et al. | |
| 2011/0119801 A1 | 5/2011 | Wright | |
| 2011/0165361 A1 | 7/2011 | Sherman et al. | |
| 2011/0279383 A1 | 11/2011 | Wilson et al. | |
| 2012/0003431 A1 | 1/2012 | Huang | |
| 2012/0183712 A1 | 7/2012 | Leonhard et al. | |
| 2012/0188743 A1 | 7/2012 | Wilson et al. | |
| 2013/0089688 A1 | 4/2013 | Wilson et al. | |
| 2014/0220283 A1 | 8/2014 | Wilson et al. | |
| 2014/0259321 A1 * | 9/2014 | Arnold | A42B 3/225 |
| | | | 2/424 |

FOREIGN PATENT DOCUMENTS

| | | |
|---|---|---|
| EP | 0671258 | 9/1995 |
| EP | 1471415 | 10/2004 |
| GB | 2310862 | 9/1997 |
| JP | 62-53832 | 3/1987 |
| JP | 4314537 | 11/1992 |
| JP | 6143496 | 5/1994 |
| JP | 7214456 | 1/1995 |
| JP | 10167765 | 6/1998 |
| JP | 2002328613 | 11/2002 |
| TW | 200700793 | 1/2007 |
| TW | 201027992 | 7/2010 |
| WO | WO0024576 | 5/2000 |
| WO | WO03052678 | 6/2003 |

OTHER PUBLICATIONS www.wikipedia.org, "Black Body", Jul. 2009, 11 pages.
www.wikipedia.org; "Infrared"; Jul. 2009; 12 pages.
www.wikipedia.org; "Pet Film (biaxially oriented)"; Jul. 2009; 4 pages.
"Declaration of Jerome Aho"; Filed Aug. 3, 2007; Case 3:07-cv-00221-Fdw-Dck; Includes: Exhibit A, Nascar Postcard (1 page), Exhibit B, 50th Anniversary Nascar letter sent Jan. 7, 1998 (1 page), and Exhibit C, Front page of "The Official Nascar Preview and Press Guide" (1 page); 9 pages.
International Search Report; International Application No. PCT/US99/95128; Date of Completion: Jan. 18, 2000; 54 pages.
International Search Report; International Application No. PCT/US02/10971; Date of Completion: Nov. 20, 2002; 3 pages.
International Search Report; International Application No. PCT/US03/16284; Date of Completion: Mar. 9, 2004; 3 pages.
Defendant's Motion for Summary Judgment; Oct. 25, 2013; pp. 1-31.
Jake Gaecke; "Appletell Reviews the iVisor for iPad"; www.appletell.com; Sep. 15, 2010 at 12:32 pm; www.technologytell.com/apple/60407/appletell-reviews-ivisor-ag-for-ipad/; 2 pages.

(56) References Cited

OTHER PUBLICATIONS www.store.moshimonde.com; "iVisor AG iPad Screen Protector"; Jul. 2010; 7 pages.
www.store.moshimonde.com; "iVisor XT Crystal Clear Protector for iPad"; Aug. 2010; 3 pages.
www.store.moshimonde.com; "iVisor AG for iPad 2 Black"; Mar. 2011; 5 pages.
www.store.moshimonde.com; "iVisor AG for !Pad 2 White"; Mar. 2011; 3 pages.
www.store.moshimonde.com; "iVisor AG for iPhone 4/4S Black"; Nov. 2010; 5 pages.
www.store.moshimonde.com: "iVisor AG for iPhone 4/4S White"; May 2010; 4 pages.
English Translation of TW201027992; "Monitor Protection Device for a Flat Panel Display"; 1 page.

* cited by examiner

ADHESIVE MOUNTABLE STACK OF REMOVABLE LAYERS

RELATED APPLICATIONS

The present application is a divisional patent application of U.S. patent application Ser. No. 14/307,189 entitled "Adhesive Mountable Stack of Removable Layers" filed on Jun. 17, 2014, the entire disclosures of which are expressly incorporated herein by reference.

TECHNICAL FIELD

The present disclosure generally relates to an adhesive mountable stack of lens layers. More specifically, the present disclosure relates to a stack of removable lens layers configured for dry mounting to optically clear eye protective surfaces.

BACKGROUND

Multilayer tear off systems can be attached to eye protective surfaces, such as goggles or face shields, with pins. In this way, pins are attached outside of the primary viewing area of the eye protector, for example, to left and right sides of the eye protector surface. To attach the system to an eye protector, the system is wrapped tightly around the optically clear lens of the eye protector by pulling the system over the pins. One example of a multilayer tear off system attached to pins of an eye protector is disclosed in U.S. Pat. No. 6,388,813, issued to the assignee of the instant application.

One issue that can arise with multilayer tear off systems relates to the propensity of dirt to accumulate between the lowest layer of the multilayer tear off system and the transparent lens of the eye protector. This accumulation of dirt can reduce visibility through the eye protector to unacceptable or undesirable levels, thereby rendering the multilayer tear off system sub-optimal or even detrimental.

Additionally, air disposed between the lowest layer of the system and the lens of the eye protector can result in undesirable reflections caused by a mismatch in the indices of refraction between lens, the system, and the air disposed therebetween. These reflections can reduce contrast and light transmission and limit the amount of light that can pass through the system and eye protector, thereby reducing the wearer's visual acuity through the eye protector.

Moreover, the pins used to secure the transparent lens of the eye protector can reduce the impact resistance of the eye protector. For example, attaching pins to the eye protector can involve drilling holes into the eye protector so that pins can be mounted therein. These holes can create points of weakness that reduce the structural integrity of the eye protector, thereby limiting the ability of the eye protector to shield against projectiles or other objects. This can be particularly significant, for example, in military applications, where the eye protectors are intended to protect a wearer against high speed projectiles or other dangerous flying debris.

Further, pins can limit the system's ability to be applied to eye protectors of varying shape, design, or style. For example, because pins are positioned at a predetermined distance from one another, the corresponding holes in the layers of the system are formed to match this predetermined distance. But as eye protectors vary in size, shape, and/or style, different eye protectors may position the pins in different locations, and at different spacing intervals. Thus, a system designed to match one eye protector may be unusable for a different eye protector.

BRIEF SUMMARY

The present disclosure describes eye protectors and methods for protecting an eye protector without significantly reducing visual acuity therethrough. In some embodiments, the eye protector has a center portion defining a center of gaze of a wearer. The eye protector can include a lens configured to protect the wearer from projectiles. The lens can have a lens refractive index (or index of refraction). The eye protector can also include an optically clear stack attached to the lens. The stack can have one or more removable layers. Each removable layer can have a removable layer refractive index. The eye protector can also include an optically clear dry mount adhesive layer attaching the stack to the lens. In some aspects, the dry mount adhesive layer forms a continuous and uninterrupted adhesive surface over at least the center portion of the eye protector. The dry mount adhesive layer can have a dry mount adhesive refractive index. In at least one aspect, the dry mount adhesive is self-wetting and attaches the stack to the lens so that air between the stack and the lens can be removed after the stack is attached and/or adhered to the lens, for example, by applying pressure across the surface of the stack. In some embodiments, the lens refractive index, the dry mount adhesive refractive index, and each removable layer refractive index are matched to within about 0.2.

The present disclosure also describes an optically clear stack configured for affixing to a lens to form an eye protector. The eye protector can have a center portion defining the center of gaze of a wearer. The lens can be configured to protect the wearer from projectiles and have a lens refractive index. The stack can include at least one optically clear removable layer, each removable layer having a removable layer refractive index. The stack can also include an optically clear dry mount adhesive layer applied to a lower surface of the stack. The dry mount adhesive layer can be configured to attach the stack to the lens and form a continuous and uninterrupted adhesive surface covering at least the center portion of the eye protector. In some embodiments, the dry mount adhesive layer is self-wetting and configured to attach the stack to the lens so that air between the stack and the lens can be removed after the stack is attached and/or adhered to the lens, for example, by applying pressure across the surface of the stack. The dry mount adhesive layer can also have a dry mount adhesive refractive index. In some embodiments, the lens refractive index, the dry mount adhesive refractive index, and each removable layer refractive index are all matched to within about 0.2.

The present disclosure also describes methods of protecting an eye protector without significantly reducing visual acuity through the eye protector. In some aspects, the eye protector can be one of the eye protectors described and depicted herein. For example, the eye protector can have a center portion defining a center of gaze of a wearer, and can include a lens (having a lens refractive index) configured to protect the wearer from projectiles. In one embodiment, the method includes selecting an optically clear stack having one or more removable layers. Each of the removable layers can have a removable layer refractive index matched to within about 0.2 of the lens refractive index. The method can also include removing a protective liner from a bottom surface of the lens stack to expose an optically clear dry mount adhesive layer. The method can also include dry mounting the stack to the lens so that the adhesive layer forms a continuous and uninterrupted adhesive layer over at least the center portion. In some embodiments, the dry mounting step can involve removing air between the stack and the lens, for example, by applying pressure to the stack and smoothing or pressing out air bubbles between the stack and the lens. The dry mount adhesive layer can be self-wetting and have a dry mount adhesive layer refractive index matched to within about 0.2 of the lens refractive index and each removable layer refractive index.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
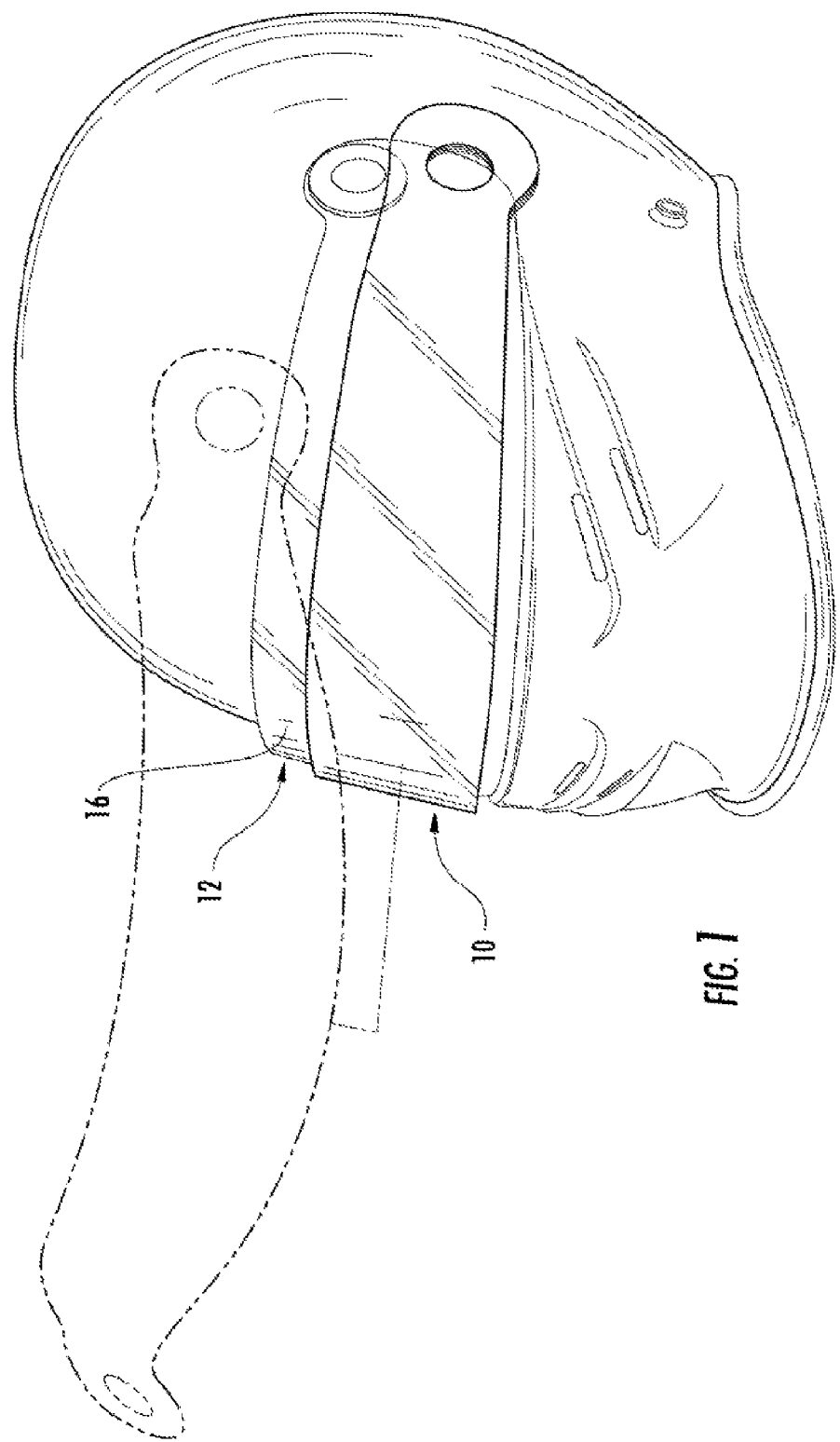
FIG. 1 is a perspective view of a helmet with an adhesive mountable stack of removable layers adhered to a lens in accordance with at least one embodiment of the present disclosure.

The present disclosure describes stacks mountable to an eye protector with an adhesive. As used throughout this specification, the term "stack" refers to a collection of one or more optically clear and/or transparent lens(es), film(s), or other layer(s) that can be attached and/or laminated together. As used herein, the phrase "optically clear" refers to a material having no perceptible visible distortion or scatter. An optically clear material may be transparent and/or colorless, but in some circumstances, a material that has a hue, shade, or a tint, for example, can be considered "optically clear" consistent with the meaning of the phrase as used herein. As used throughout this application, "eye protector" refers to optically clear objects designed to provide protection to the eyes and/or face of a wearer. "Eye protector" can refer to eye shields, face shields, lenses, glasses, masks, goggles, visors, windows, or the like. Moreover, where a particular eye protector is referenced (e.g., a face shield) in a described example, it is contemplated that other eye protectors (e.g., goggles) can be reasonably substituted in place of the eye protector without deviating from the scope of the disclosure, unless the context of the disclosure suggests otherwise.

Embodiments of the present disclosure provide systems for maintaining or restoring visibility through eye protectors during use while maintaining and/or maximizing visual acuity. The system may comprise a single transparent layer or a plurality of transparent layers adhered to each other and to a transparent lens of the eye protector. Although various aspects disclosed herein relate to a stack having two or more removable layers, some aspects disclosed herein may also be applicable to an embodiment having a single transparent layer. The uppermost layer of the stack can be peeled off from the next lower layer and/or the transparent lens of the eye protector to improve and/or restore visibility through the eye protector. The transparent lens of the eye protector, the removable transparent layers of the stack, and the adhesive that attaches the layers of the stack to each other and the stack to the transparent lens may each define refractive indices that are within 0.2 of each other. This can serve, for example, to limit, reduce, and/or eliminate perceptible internal reflections through the system, or to otherwise generally improve or maintain visibility through the system. Also, by adhering the lowest layer of the stack of the transparent lens with an optically clear uninterrupted layer of adhesive, the strength, integrity, and/or durability of the transparent lens of the eye protector may not be diminished, which can occur, for example, when pins are installed through the eye protector to assist with the mounting of removable layers. Moreover, the uninterrupted layer of adhesive can provide a physical barrier that inhibits, thwarts, limits, reduces, and/or prevents dirt or debris from entering and accumulating between the lowest layer of the stack and the transparent lens.

Some embodiments of the present disclosure describe a face shield. The face shield can include a first transparent lens, a stack of two or more removable transparent layers, a dry mount adhesive layer, and one or more optically clear stack adhesive layers. The first transparent lens can be disposed in front of a wearer's eyes, for example, to protect the wearer's eyes from impact. The transparent lens may define a first refractive index (or a lens refractive index), and each layer of the stack may define a removable layer refractive index. The dry mount adhesive layer can be disposed between the first transparent lens and a lowest layer of the stack so that the stack is affixed or affixable to the first transparent lens. The dry mount adhesive layer may be continuous and uninterrupted. In some embodiments, an outer periphery of the dry mount adhesive layer covers a center of gaze of a wearer. The dry mount adhesive layer may define a dry mount adhesive refractive index. The stack adhesive layers may be interposed between each pair of transparent layers of the stack so that an uppermost layer of the stack is removable from the stack. Each optically clear stack adhesive layer may define a stack adhesive refractive index. The refractive indices of the lens, the dry mount adhesive, each removable layer of the stack and each adhesive layer of the stack may be within about 0.2 of each other. In some embodiments, these refractive indices are matched within an even smaller range, for example, within 0.1, 0.05, or 0.02.

The first transparent lens can be or comprise a polycarbonate material. The dry mount adhesive layer can be or comprise an acrylic polymethyl methacrylate material or a high index silicone adhesive. The removable layer(s) can be or comprise a polyethylene terephalate material. The stack adhesive layers can each be or comprise an acrylic polymethyl methacrylate material or a high index silicone adhesive.

In some embodiments, the transparent lens can be a face shield of a helmet, a lens of an eyeglass or a face shield of a goggle.

In some examples, opposed outer portions of the stack define outer edges in a stepped format. In some aspects, the opposed outer portions are adhesive free.

Referring now to the drawings, FIG. 1 shows a system for restoring visibility through an eye protector 12 while maintaining visual acuity therethrough. The stack can include a single removable transparent layer or a plurality of removable transparent layers (e.g., 2-7 layers) attachable to the eye protector 12, such that the layers and peeled off one-by-one as individual layers when needed.

The stack 10 can be adhesively mountable to the eye protector 12, for example, using a dry mount adhesive that facilitates mounting of the stack 10 to the lens 16. In some embodiments, the dry mount adhesive can be self-wetting, and can facilitate the removal of air between the stack 10 and the lens 16 after mounting. For example, because the dry mount adhesive is self-wetting, a user can remove air pockets or air bubbles that form between the stack 10 and the lens 16 by applying pressure to the stack 10 and smoothing or spreading pressure outwardly towards the edges of the stack 10. In this manner, a user may be able to reduce, limit, and/or eliminate perceptible air pockets between the stack and the lens 16 after mounting.

In some embodiments, the refractive indices between the transparent lens 16, the dry mount adhesive layer 18a, the removable layers 14a-n of the stack 10, and the interposed stack adhesive layers (18b and 18c) are all matched to within about 0.2 of each other. As a result, additional internal reflections through the eye protector 12 can be significantly limited, reduced and/or eliminated from the wearer's perspective.

Figure 3:
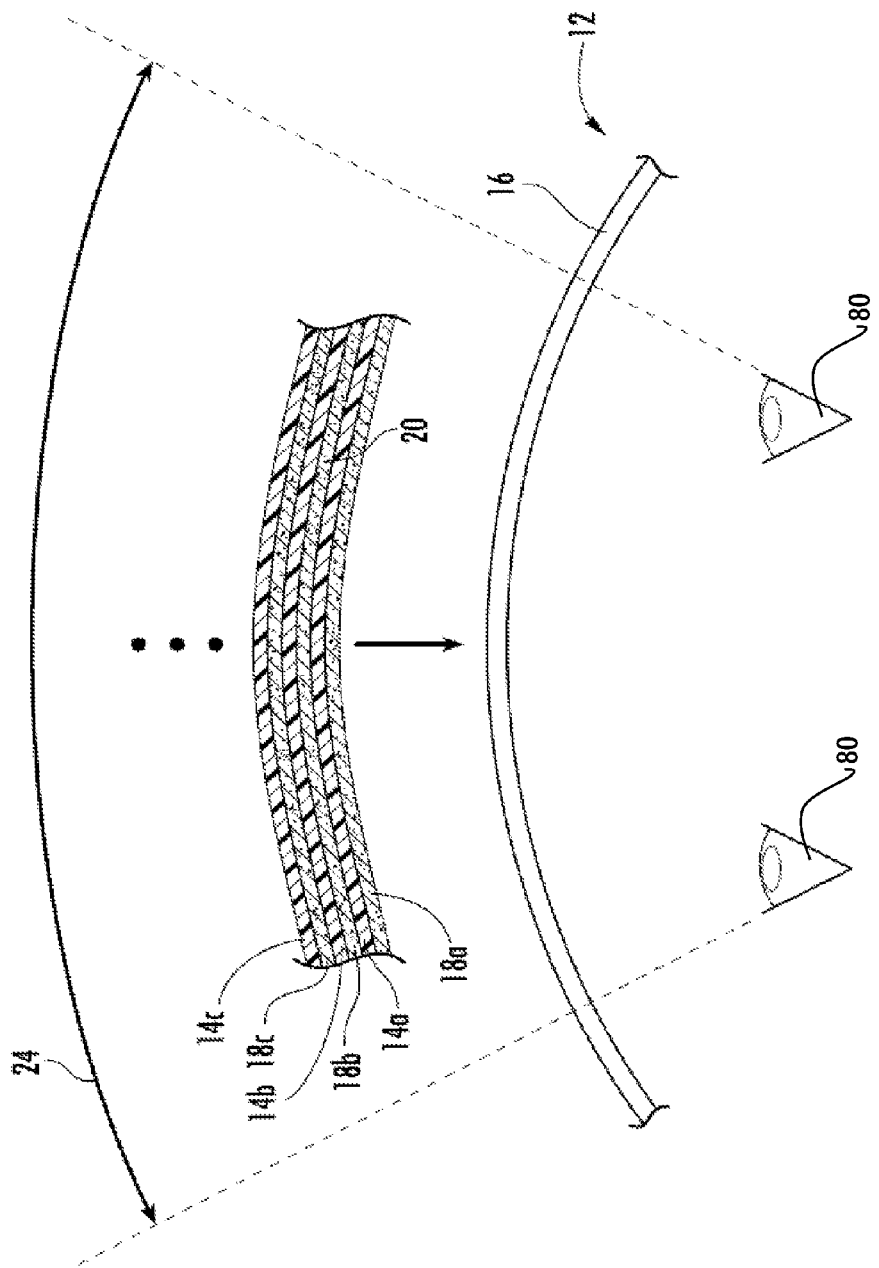
FIG. 3 is a cross-sectional view of a stack and lens of an eye protector in accordance with at least one embodiment of the present disclosure.

As shown in FIG. 3, the dry mount adhesive layer can be optically clear, and may form a continuous, uninterrupted dry mount adhesive layer 18a that allows for the stack to be dry mounted to the lens 16 of the eye protector 12. Dry mounting refers to an adhesive that exhibits adhesive properties upon removal of a protective liner without requiring liquid or heat activation. Using a layer of adhesive 18a to mount the stack 10 to the eye protector 12 creates a physical barrier that inhibits, thwarts, limits, and/or prevents dirt, dust, and/or debris from accumulating between the lowest layer 14a of the stack 10 and the transparent lens 16 of the eye protector 12. Thus, the system can maintain visibility through the eye protector 12 even when used in dusty and dirty terrain. Also, using dry mount adhesive layer 18a to secure the stack 10 to the eye protector 12 helps maintain the strength of the lens 16 of the eye protector 12. That is, the integrity of the lens 16 need not be diminished, for example, by drilling holes in the lens to mount pins, as is sometimes done with other systems.

The layer of adhesive 18a can be selected to help limit, reduce, and/or eliminate air in between the top surface of the lens 16 and the lower surface of the lowest layer 14a of the stack 10. For example, the adhesive layer 18a can be selected as a self-wetting dry mount adhesive that allows the stack 10 to first be applied to the lens 16, and then smoothed or evened out, for example, by applying pressure to remove air bubbles or pockets without the use of water or other liquids. The dry mount adhesive can be selected to have material properties that allow any air bubbles or air pockets forming between the stack 10 and the lens 16 to be worked out relatively easily by a user. Moreover, because water or other fluids are not necessary (e.g., because the dry mount adhesive is self-wetting), the adhesive can dry and adhere to the lens relatively quickly (e.g., instantly or nearly instantly), thereby inhibiting, limiting, or preventing the stack 10 from moving, sliding, or delaminating from the lens 16.

The dry mount adhesive can also be selected to have properties that allow the lowest layer of the stack 10 to adhere to the lens 16 with a peel strength that is greater than the peel strength between each successive layer of the stack 10. In this manner, the dry mount adhesive can maintain a secure attachment between the stack 10 and the lens 16 even when an upper layer of the stack 10 is being peeled away or otherwise removed by a user. In some embodiments, the dry mount adhesive layer provides a peel strength sufficient to prevent the stack 10 from sliding, moving, or delaminating from the lens in the face of high wind speeds. For example, in some aspects, the dry mount adhesive is selected so that it can be effectively applied to prevent delamination from the lens of a windshield or face shield worn by racers that may face wind speeds in excess of 100 or 200 miles per hour. The dry mount adhesive can also be selected to provide a peel strength that avoids adhesion transfer; that is, the peel strength can be low enough to avoid leaving behind an adhesive residue when the stack 10 is peeled away from the lens 16.

The dry mount adhesive can also be selected to have an optical clarity, or haze level that is less than 1.0%, and a light transmission value of greater than 99%. The dry mount adhesive can be selected to be capable of wetting to the surface of the lens 16 without forming bubbles between the stack 10 and the lens (or in a manner that allows the bubbles to be readily removed). The dry mount adhesive can also be selected to have high temperature, humidity, and UV resistance. In some embodiments, the dry mount adhesive will be selected to have non-yellowing properties.

In some embodiments, the dry mount is selected to have some or all of the properties described above, while also having a refractive index that matches the refractive index of the lens 16, the removable layers 14 of the stack 10, and/or the stack adhesive layers (18b and 18c) laminating the layers 14 of the stack 10 together.

It has been surprisingly discovered that a polymethyl methacrylate adhesive (PMMA) can serve as a dry mount adhesive that satisfies all of these specifications. That is, PMMA can be used as a dry mount adhesive that satisfies the peel strength specifications while also offering a refractive index that can be matched within 0.2 of the refractive indices of suitable lens materials (e.g., polycarbonate), and suitable removable layer materials (e.g., PET) and suitable stack adhesive layers. For example, in some embodiments, the refractive index for PMMA can be about 1.492. PMMA can also satisfy the specifications relating to optical clarity/haze, light transmission, wetting properties, bubble prevention/removal capabilities, temperature resistance, humidity resistance, UV resistance, and non-yellowing properties. Thus, the dry mount adhesive layer can be a PMMA configured to satisfy some or all of these specifications, thereby facilitating dry mounting of the lowest layer 14a of the stack 10 to the lens 16.

The thickness of the dry mount adhesive layer 18a can vary depending on the use. For example, in some embodiments, the dry mount adhesive layer 18a can be between about 10 microns and 20 microns, or more specifically between 13 microns and 17 microns, or even more specifically, about 15 microns thick (i.e., 15 µm).

The peel strength of the dry mount adhesive can be configured to correlate with the peel strength of the adhesive holding the layers 14 of the stack 10 together. For example, in some embodiments, the peel strength of the dry mount adhesive may be relatively high when compared to the peel strength of the adhesive holding the layers 14 of the stack 10 together to ensure that the stack remains attached to the lens 16 when the various layers 14 of the stack 10 are removed or peeled away. It should be noted, however, that using an adhesive that offers a peel strength that is too high can present drawbacks. For example, where a stack or a removable layer is mounted to a lens with a peel strength that is greater than about 100 grams (measured at a 180° peel test at 12 inch per minute rate), there can be a significant risk of adhesive transfer. That is, where the peel strength is too high, removing the layer or stack can cause the adhesive layer to fracture, thereby leaving behind a residual portion of the adhesive on the lens of the eye protector. This adhesive residue can occlude or impair the visibility through the lens, and can also make the process of mounting another stack or layer on the lens difficult, inefficient, and/or impossible. Thus, in some embodiments, a dry mount adhesive material is selected and configured so that it provides a peel strength high enough to maintain the stack 10 attached to the lens 16 when the upper layers 14 are peeled away, but low enough to allow the stack 10 to be removed from the lens 16 without leaving behind residual adhesive.

The correlation between the peel strength of the dry mount adhesive layer and the peel strength of the adhesive holding the layers 14 of the stack 10 together can depend upon how the stack 10 is mounted to the lens 16. For example, where the stack 10 is intended to be dry mounted to a lens 16 without the use of pins or posts applying tension to the stack, it can be useful to use a dry mount adhesive that offers a peel strength that is about twice the peel strength necessary to remove the removable layers 14 of the stack 10. In some embodiments, the peel strength for each of the removable layers 14 can be between about 10 grams and about 50 grams when measured using a 180° peel test at a 12 inch per minute rate, with an average peel strength of about 25 grams to about 30 grams for each layer 14. Thus, in such an embodiment, the dry mount adhesive can be selected to have a peel strength of about 50 grams to about 60 grams, i.e., about twice that of the average peel strength of the removable layers 14.

As another example, where the stack 10 is intended to be dry mounted using pins or posts for tension, the peel strength of the dry mount adhesive may be equal to, or even less than that of the removable layers 14. Because the tension of the pins and/or posts can help maintain the position of the stack 10 on the lens 16 when the removable layers 14 are peeled away, the adhesive strength attaching the stack 10 to the lens 16 need not be quite as high. Thus, in such an example, as long as the dry mount adhesive provides sufficient tack to establish "wetting" to the lens of the eye protector without forming air bubbles, the dry mount adhesive peel strength may be sufficient. It has been surprisingly and unexpectedly discovered that a PMMA adhesive can be configured to meet these peel strength specifications. And as noted above, PMMA can also meet the other specifications desirable for adhering a stack 10 to a lens 16.

Other types of adhesive materials are also contemplated for the dry mount adhesive layer 18a. By way of example and not limitation, the dry mount adhesive layer 18a may be a "high index" dry mount silicone adhesive. The high index dry mount silicone adhesive may have a refractive index between about 1.45 to 1.54. The dry mount adhesive layer 18a may be provided in various form factors for pre-application onto the lowest layer 14a such as liquid, spray on or film. In some embodiments, the dry mount adhesive layer 18a can facilitate the dry mounting of the stack 10 to the transparent lens 16 (e.g., mounting without water or fluid). In some embodiments, however, the dry mount adhesive layer 18a can (additionally and/or alternatively) be activated with a fluid or liquid (e.g., water), or heat.

The dry mount adhesive layer 18a may be applied to the bottom surface 20 of the lowest layer 14a by pouring the liquid adhesive over the bottom surface and letting the liquid spread over the bottom surface 20 of the lowest layer 14a. Alternatively, the dry mount adhesive may be sprayed over the bottom surface 20 of the lowest layer 14a. As a further alternative, the dry mount adhesive may be provided as a film and be laminated on the bottom surface 20 of the lowest layer 14a. At the time of attaching the stack 10 to the eye protector 12, the protective liner can be removed from the dry mount adhesive layer 18a. In operation, pressure can be applied to the stack 10 against the lens 16 of the eye protector 12 to adhere stack 10 to the eye protector 12. In some embodiments, the dry mount adhesive 18a can be pre-applied to the bottom surface 20 of the lowest layer 14a and then covered with a protective liner to prevent contamination of the dry mount adhesive layer 18a prior to mounting of the stack 10 to the eye protector 12 of the helmet.

Figure 2:
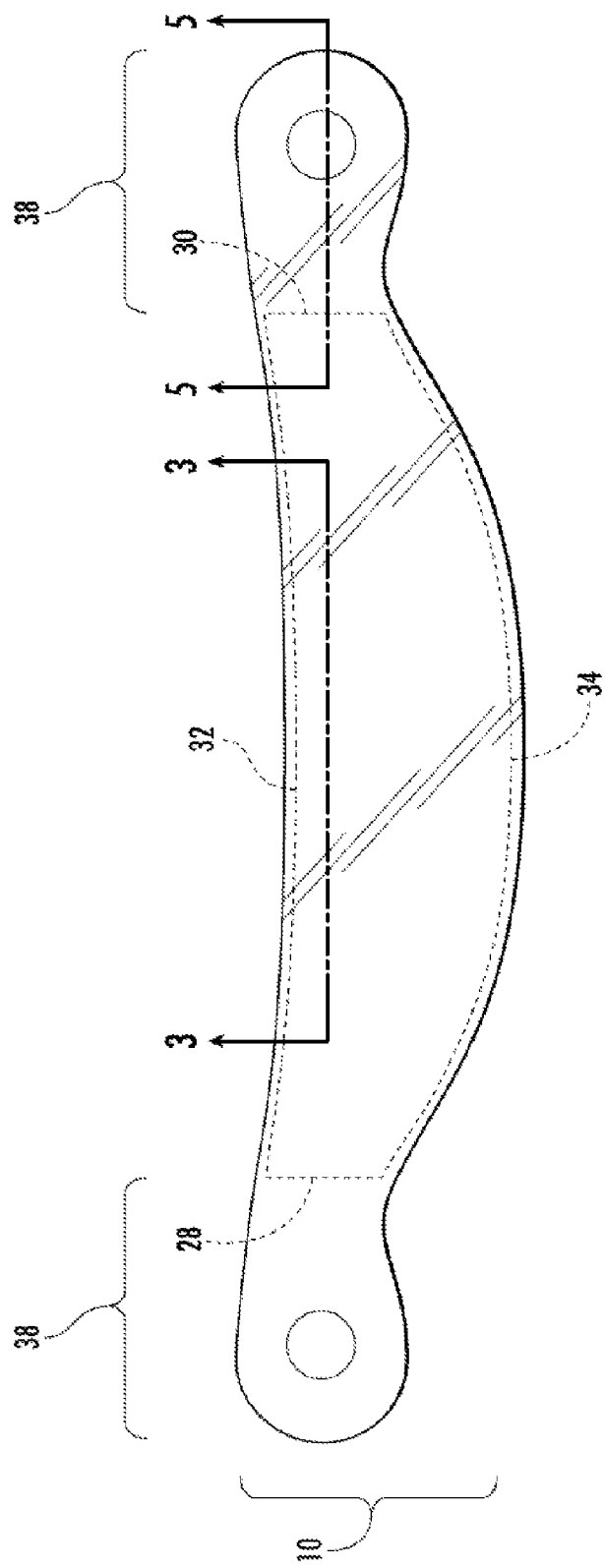
FIG. 2 is a front view of a stack in accordance with at least one embodiment of the present disclosure.

The layers 14 of the stack 10 may be oversized with respect to the eye protector 12. In some aspects, a user may cut the stack 10 of fit an eye protector 12 so that one size may fit a plurality of different eye protectors 12. Alternatively, the stack 10 can have an outer periphery that has been pre-cut to fit a particular eye protector. An example of one such configuration is shown in FIG. 2. However, other configurations of pre-cut stacks 10 of layers 14 are also contemplated.

Referring again to FIG. 1, a stack 10 may be mounted to an eye protector 12 (e.g., a face shield, eye shield, or visor) of a helmet, as shown. Although various embodiments and aspects described herein relate to a face shield of a helmet, it is also contemplated that the stack 10 may be mounted to other types of eye protection devices such as goggles (e.g., ski goggles, snowboard goggles, motocross goggles), glasses (e.g., combat eyewear, sunglasses, prescription glasses), face shields for dentistry, medical hoods, welding masks, and the like. Additionally, the stack 10 may be mounted to a video display (e.g., a television screen, a computer monitor, a tablet device, a smart phone device, etc.), a touch sensitive screen, a window, or windshield. The various embodiments and aspects described herein may be applied to other structures and devices.

FIG. 3 shows a cross-sectional view (cut along line 3-3 of FIG. 2) of the stack 10 and the lens 16 of an eye protector 12. The transparent lens 16 of the eye protector 12 can be fabricated from a polycarbonate material. In some embodiments, the refractive index for polycarbonate material can be between about 1.55 and about 1.65. More specifically, the refractive index of the polycarbonate material can be between about 1.58 and 1.59. Even more specifically, the refractive index of the polycarbonate material can be about 1.5849. The bottom surface 20 of the stack 10 (i.e., the bottom surface of the lowest removable layer 14a of the stack 10) may have a dry mount adhesive layer 18a disposed thereon for securing the stack 10 to the top surface 22 of the lens 16. The dry mount adhesive layer 18a can be optically clear and/or transparent and can define a refractive index. The refractive index of the dry mount adhesive layer 18a may be about equal to the refractive index for the eye protector 12. More particularly, the refractive index for the dry mount adhesive layer 18a may be within about 0.2 of the refractive index for the lens 16. If the lens 16 is fabricated from a polycarbonate material, then the adhesive layer 18a may be selected so that its refractive index is between about 1.7849 and 1.3849. In some embodiments, the selected dry mount adhesive layer 18a will have the refractive index as described, while also having material properties allowing the stack 10 to be dry mounted to the lens 16 such that air bubbles can be pressed out after mounting, and while maintaining a peel strength that allows the stack 10 to maintain a bond with the lens 16 in spite of the removal of upper layers 14 of the stack 10, and in the face of high wind speeds.

Refraction is a change in direction in which waves travel when they pass from one medium into another. Light waves are refracted (i.e., bent) when they pass at an angle from one medium into another because the velocity of light is different in each of the mediums. The amount that a ray of a certain wavelength bends in passing from one medium into another is indicated by the refractive index between the two mediums for that wavelength. The refractive index indicates the amount that the light ray bends as it passes out of one medium into another. When light passes from air into a denser material (e.g., transparent film or lens), the speed of the light decreases. When light enters the denser material at an angle other than a right angle, this decrease in the speed of light causes the light ray to bend at the point of entry. This bending is referred to as refraction.

The refractive index of a medium (also referred to as the index of refraction) is a dimensionless number representing the ratio between the speed of light in a vacuum and the speed of light in the medium. That is, the refractive index n of a substance can be written as $n=c/v$, where c is the speed of light in a vacuum (about 299,792,458 meters per second), and v is the speed of light in the substance. For example, the refractive index of water (at about 20° C.) can be about 1.33, meaning that light travels 1.33 times slower in water than it does in vacuum. Further, the refractive index of air can be about 1.000293, meaning that light travels 1.000293 slower in air than it does in a vacuum. The refractive index determines the angle at which light is bent, or refracted, when passing from one material to another. The ratio of refractive indices between two mediums is also relevant to the amount of light that is internally reflected when light passes from one medium to the other. Thus, when combining or attaching multiple layers of optically clear material together, the ratio of refractive indices between the two mediums will determine the amount of light that is internally reflected between the mediums away from the eyes of the wearer. Accordingly, the greater the mismatch between two mediums attached to one another, the less light will be able to pass through the combined materials to the eyes of the wearer.

The dry mount adhesive layer 18a may be disposed on the bottom surface 20 of the lowest layer 14a in a continuous uninterrupted fashion (e.g., without perceivable breaks or gaps in the adhesive layer). In one example, the dry mount adhesive layer 18a is applied to cover a viewing angle 24 through the eye protector 12, where the viewing angle 24 generally defines a range of vision of the eyes 80 of the wearer. The left and right edges 28, 30 and the top and bottom edges 32, 34 (see FIG. 2) of the dry mount adhesive layer 18a may cover the viewing angle 24 through the eye protector 12 when the stack 10 is mounted to the lens 16. The viewing angle 24 may correspond to the outer limits of the continuous, uninterrupted dry mount adhesive layer 18a which may extend to or beyond the center of gaze of the eyes 80 of the wearer of the eye protector 12.

Depending on the intended use of the eye protector 12, the viewing angle 24 defined by the coverage of the dry mount adhesive layer 18a may increase or decrease as desired. By way of example and not limitation, the continuous uninterrupted coverage of the dry mount adhesive layer 18a may be sufficiently large so that the dry mount adhesive layer 18a extends beyond the near peripheral vision, mid peripheral vision or far peripheral vision with the stack 10 mounted to the eye protector 12. In other words, when a wearer is wearing an eye protector 12 with a stack 10 mounted thereon, the dry mount adhesive layer 18a can be configured to at least cover all or a portion of the center of gaze of the wearer. Optionally, the continuous uninterrupted coverage of the dry mount adhesive layer 18a may be larger to cover the center of gaze of the wearer plus the near peripheral vision and beyond to the mid-peripheral vision and even as far as the far peripheral vision.

In some embodiments, the stack 10 may be mounted to the eye protector 12 so that no perceivable air, or virtually no perceivable air, is trapped between the lowest layer 14a and the lens 16 of the eye protector 12.

The stack 10 may have a plurality of transparent layers 14a-n stacked upon each other. In one example, the layers 14a-n may be fabricated from a transparent film or lens. The film may be polyethylene terephthalate (PET), which may a refractive index of about 1.57 to about 1.67, for example.

The plurality of layers 14a-n may be removably attachable to each other with an interposed adhesive layer (e.g., 18b and 19c). In one example, the interposed adhesive 18b, 18c may be the same type of adhesive applied to the bottom surface 20 of the lowest layer 14a. In this example, the interposed adhesive 18b may have a refractive index of about 1.492 if a PMMA adhesive is used or between about 1.45 to 1.54 if a high index adhesive is used, as mentioned above. In some embodiments, the interposed adhesive 18b may be another optically clear adhesive, provided that the refractive indices of the interposed adhesive 18b, dry mount adhesive layer 18a, transparent lens 16 and the layers 14 are all within 0.2 of each other. Thus, if the lens 16 is fabricated from a polycarbonate material having a refractive index of about 1.5849, and the layers of the stack 10 are fabricated from a PET having a refractive index of about 1.62, then the dry mount adhesive layer 18a may be selected so to have a refractive index is between about 1.7849 and 1.42 so as not to deviate by more than 0.2 from the refractive indices of the lens 16 and the layers 14 of the stack 10, respectively. And in some embodiments, the dry mount adhesive layer 18a will be selected to have the refractive index as described, while also having other material properties described above (i.e. peel strength, self-wetting, allowing for removal of air, etc.).

The adhesive 18b interposed between any two layers 14 may be coextensive with the dry mount adhesive layer 18a on the bottom surface 20 of the lowest layer 14a. In this regard, the coverage of the interposed adhesive 18b can be sufficiently large, continuous and uninterrupted so that the interposed adhesive 18b covers the entire center of gaze of the person, or center of gaze plus the near peripheral vision, mid peripheral vision or even as far as the far peripheral vision through the eye protector 12. In some embodiments, the interposed adhesive 18b may be disposed between the layers 14a-n so that no air, or virtually no air, is perceivably trapped between the upper and lower layers 14 of the stack 10.

As shown in FIG. 2, the interposed adhesive 18b may extend to the very edge of the layers 14a-n except for the lateral end portions 38. The lateral end portions 38 of the layers 14a-n may thus be adhesive free, thereby providing an area for a wearer to grasp and peel off the uppermost layer 14a-n to expose a clean lower layer 14 or the lens 16 of the eye protector 12.

Referring again to FIG. 3, the stack 10 may have three layers (14a, 14b, and 14c); however, it is contemplated that the system may have one or more layers 14a-n (e.g., seven layers 14). When a wearer tears off the uppermost layer 14c, the interposed adhesive layer 18c can be pulled off and removed from the next lower layer 14b. The interposed adhesive 18c can remain with the uppermost layer 14c that has just been removed. To this end, the bottom surface of the uppermost layer 14c and/or the top surface of the lower layer 14b may be treated so that the interposed adhesive 18c has a lower peel strength to the top surface of the lower layer 14b compared to the bottom surface of the top layer 14c. Additionally, the peel strength of the interposed adhesive 18 may be greater between higher pairs of layers 14 compared to the peel strength of the interposed adhesive 18 between lower pairs of layers 14. By way of example, the force required to peel off layer 14b from layer 14a may be greater than the force required to peel off layer 14c from layer 14b. In this manner, peeling off the uppermost layer 14c, does not cause the layer 14b immediately below the uppermost layer 14c to delaminate from the stack 10. The layers 14a and 14b, therefore, can remain with the stack 10 attached to the eye protector 12 after removing or peeling off layer 14c. Further, the peel strength should also be such that removal of the layer 14 or stack 10 does not leave behind residual adhesive on the surface of the lens 16. That is, the peel strength can be low enough so that the adhesive layer remains attached to the layer that has been peeled away. Although the peel strength between upper and lower pairs of layers 14 is contemplated as varying, it is also contemplated that the peel strengths between upper and lower pairs of layers 14 may be equal to each other. In some embodiments, the peel strength between the layers can be about 10 grams to 50 grams, with an average peel strength between about 25 grams and about 30 grams, measured using a 180° test at a rate of 12 inches per minute.

Figure 5:
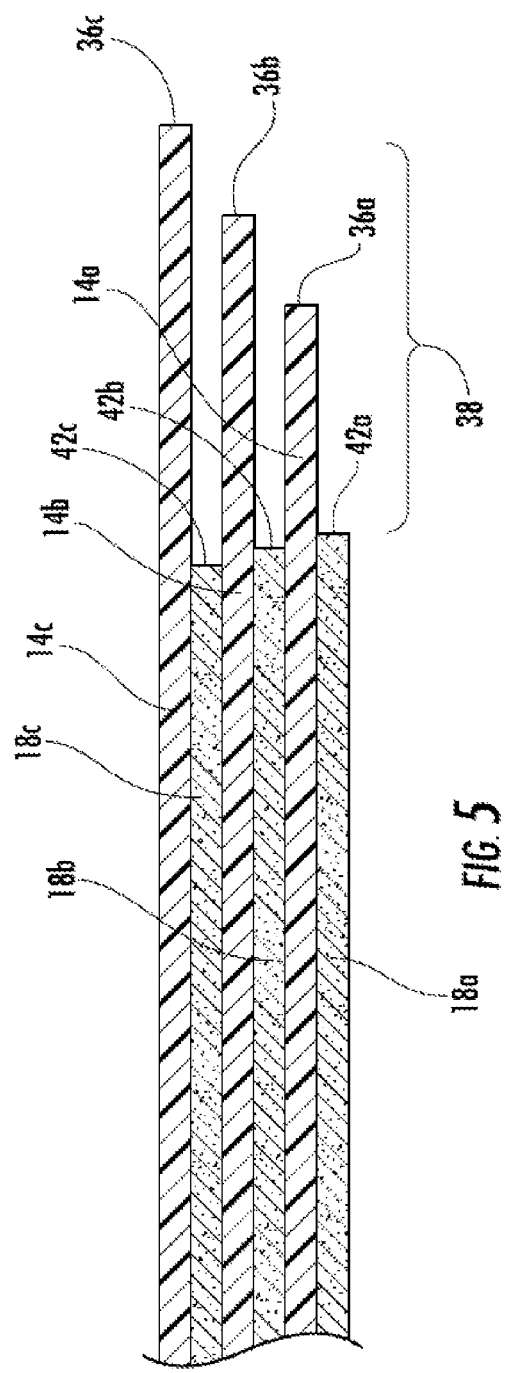
FIG. 5 is a cross-sectional view of a stack with progressively stepped layers to facilitate gripping of the uppermost layer of the stack in accordance with at least one embodiment of the present disclosure.

To further facilitate removal of a layer 14 individually or one by one, the stack 10 can include an outer edge 42 of the adhesive layer 18 that is progressively offset outward between each successive lower pairs of layers 14, as shown, for example, in FIG. 5. By way of example and not limitation, the adhesive layer 18c between an upper pair of layers 14c and 14b may define an edge 42c. The outer edge 42b of the next lower adhesive layer 18b may be positioned slightly outward from the immediately upper adhesive layer 18b. The dry mount adhesive layer 18a disposed on the bottom surface of the lowest layer 14a may have an edge 42a that is disposed even further outward compared to the outer edge 42b of the middle adhesive layer 18b. This outward progression facilitates removal of only the uppermost layer one by one. In this aspect, the peel strength is preferably progressively stronger between lower pairs of layers 14 but it is also contemplated that the peel strengths between upper and lower pairs of layers 14 are equal to each other. The positioning of the outer edges 42 of the adhesive layer 18 facilitates removal of the uppermost layer one by one, as it allows a wearer to discern between the various layers, and readily grab and separate one layer 14 of the stack 10 (in particular, the uppermost layer) from the others.

Figure 4:
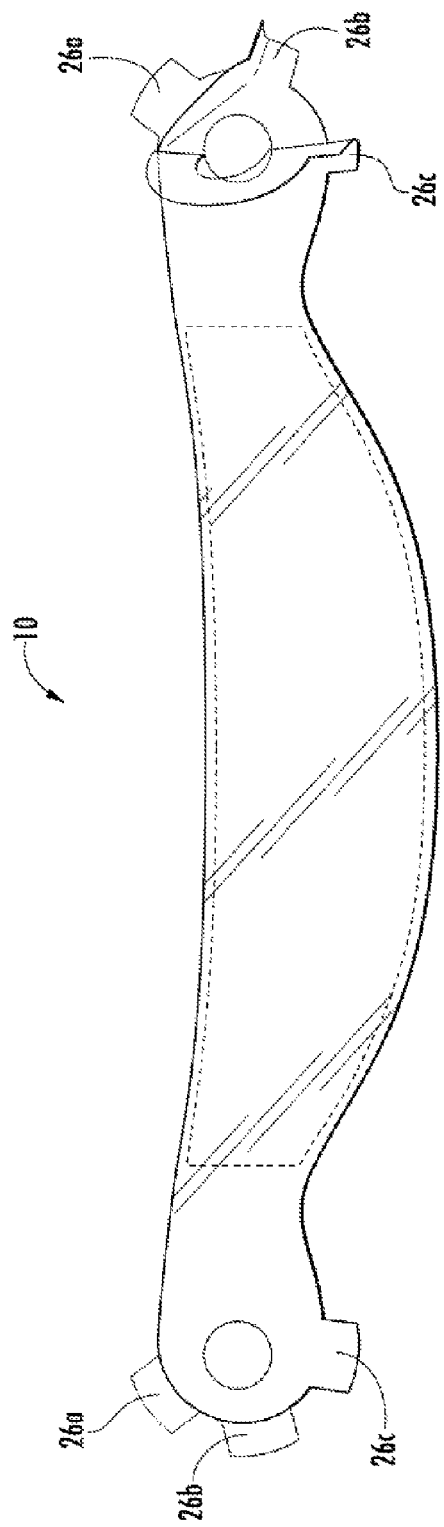
FIG. 4 is a front view of a stack with a plurality of offset tabs to facilitate removal of an uppermost layer of the stack in accordance with at least one embodiment of the present disclosure.

Referring to FIG. 4, the stack 10 may have tabs 26a-n that extend out from the opposed end portions of the transparent layers 14a-n. FIG. 4 shows the layers 14a-n on the right side of the stack 10 being peeled slightly upward to demonstrate that tab 26c can be used to peel off the top layer 14c, tab 26b can be used to peel off the middle layer 14b, and tab 26a can be used to peel off the lowest layer 14a. The tabs 26a-n may be sufficiently large for the person's index finger and thumb to grasp and pull off the uppermost layer 14 during use. The tabs 26a-n may be radially offset for each successive lower layer 16 to provide an intuitive tab removal system as shown in FIG. 4. Additionally and/or alternatively, the tabs 26a-n may be linearly offset. In FIG. 4, the tabs 26a-n are radially offset from an adjacent tab 26 of the immediately upper or lower layer 14.

In use, a wearer can grasp the tab 26c and peel off the uppermost layer 14c when the uppermost layer 14 is soiled or visibility through the stack 10 is reduced to an unacceptable level. When visibility through the stack 10 is again reduced to an unacceptable level, the wearer can grasp tab 26b to remove the next uppermost layer 14b. The process can be repeated until the last layer 14a is removed by grasping and peeling off the last layer 14 which is adhered to the transparent lens 16 of the eye protector 12. Thus, the stack 10 can be configured such that each of a plurality of removable layers 14 can be removed to expose a clean and relatively clear viewing surface.

Referring again to FIG. 5, which shows a cross section of the stack cut along line 5-5 of FIG. 2, the layers 14a-n of the stack 10 may be adhered to each other so that the end portions are configured in a stepped manner. The layers 14 of the stack 10 may each have an outer edge 36a-n. The outer edge 36c of the uppermost layer 14c may extend out further than the outer edge 36b of the lower layer 14b. To peel off the uppermost layer 14c, the wearer can grasp the outer portion of layer 14c by indexing his or her fingers with the outer most edge 36c. The wearer may then pull up on the outer portion 38 of the layer 14c to remove the uppermost layer 14c off of layer 14b. In some embodiments, the outer portion 38 of the layer 14c will not have adhesive so that the user may grasp the outer portion 38 of layer 14c.

Figure 6:
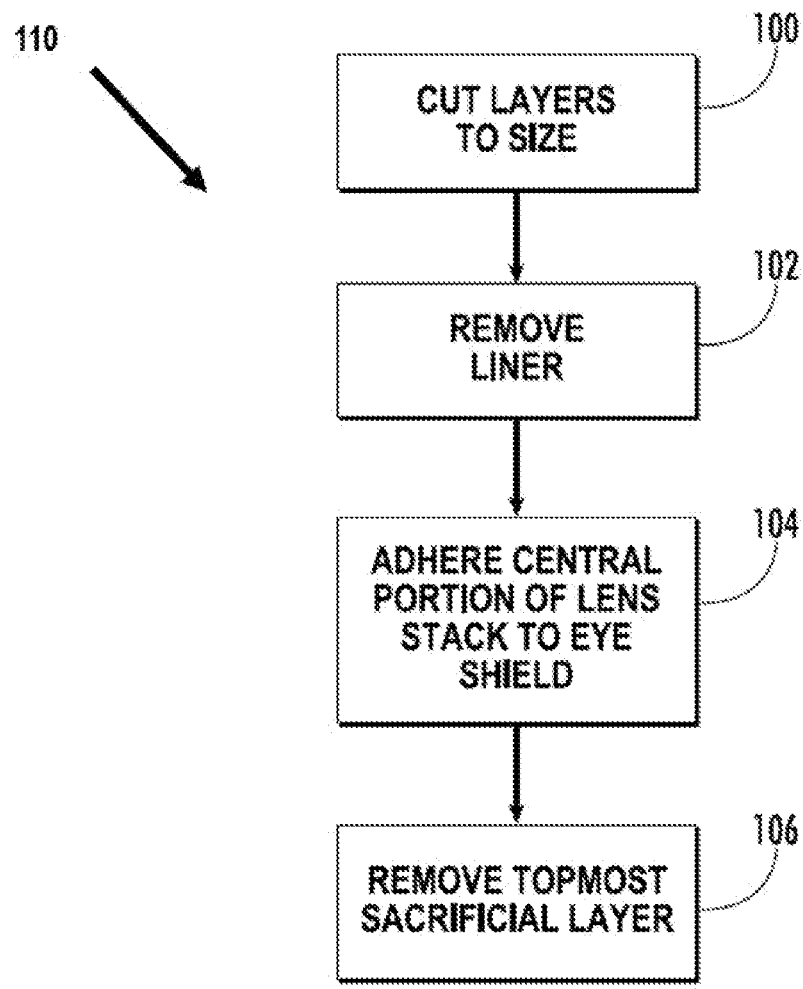
FIG. 6 is a flow chart of a method for mounting a stack to an eye protector in accordance with at least one embodiment of the present disclosure.

The present disclosure also provides methods and processes for mounting a stack (e.g., stack 10) to an eye protector, and for protecting an eye protector (e.g., eye protector 12) without significantly reducing visual acuity through the eye protector. FIG. 6 is a flow diagram of an example process 110 for mounting a stack to an eye protector. At step 100, the stack can be formed, for example, by cutting the layers of the stack to fit the size of the eye protector. In some embodiments, step 100 can also include laminating the layers of the stack together with an adhesive, for example, a high index silicone adhesive. Step 100 can also include applying a dry mount adhesive layer to a lower surface of the stack (e.g., a PMMA adhesive), and providing a protective liner over the dry mount adhesive. At step 100, the adhesive can be selected to have material properties sufficient to match the refractive index of the adhesive with the refractive indices of the lens and the removable layers of the stack within about 0.2, and that demonstrates adhesive properties described herein with respect to peel strength, self-wetting, and/or dry mounting, for example.

After cutting the stack, a protective liner can be removed from the lowest layer of the stack to expose a dry mount adhesive (e.g., dry mount adhesive layer 18a described herein) at step 102. Removal of the protective liner can expose the dry mount adhesive and thus prepares the stack for dry mounting to the eye protector. In some embodiments, the protective liner can be removed prior to cutting of the stack.

With the adhesive exposed, the lowest layer of the stack can be adhered and/or attached to the lens (e.g., lens 16 as described herein) of the eye protector at step 104. In some aspects, step 104 can include mounting portions of the stack to corresponding protrusions or pins on the eye protector to assist in the support process. However, in some embodiments, the stack can be applied directly to the lens without the use of pins or other mounting assistance techniques.

In some embodiments, step 104 also includes removing air bubbles or air pockets between the lowest layer and the eye protector. For example, at step 104, most, or even all of the air bubbles or air pockets can be removed. This can be accomplished, for example, by applying a pressure to the surface of the stack and moving that pressure towards the edges to push out the air bubbles or air pockets. For example, the air bubbles can be removed with the assistance of a finger, a squeegee, a card, or another rigid surface that can help to press and move the air bubbles to the edge of the stack. This can be facilitated if the dry mount adhesive is self-wetting. For example, the dry mount adhesive can be a PMMA or other self-wetting material that maintains a bond between the stack and the eye protector, while allowing air that forms therebetween to be removed.

During use, visibility through the eye protector may be unacceptably reduced through soiling or damage to the uppermost layer, for example, by splattering of fluids and debris (e.g., mud, dirt, water, etc.). In this manner, at step 106, the method can include removing the uppermost layer of the stack, one-by-one, as described above. In this way, the dry mount adhesive adhering the stack to the eye protector can form a peel strength that is strong enough to maintain the attachment of the stack to the eye protector even when the uppermost layer of the stack is being removed.

Embodiments of the system disclosed herein have been described in relation to a stack of three removable layers (e.g., layers 14a, 14b, and 14c). However, it is also contemplated that the system 10 may have more or fewer than three layers. For example, some embodiments of a stack may have one or two layers, and other embodiments may have four, five, six, seven, or more layers, as desired.

The thickness of the layers of the stack and/or adhesive can also vary depending on the intended use. For example, in some embodiments, each of the layers of the stack may have a thickness of between about 0.0005 inches (i.e., half a mil) to about 0.014 inches (i.e., 14 mils). In some embodiments, depending on the intended use, the number of layers used, and other considerations, the layers may have a greater or smaller thickness. Further, in some embodiments, the thickness of each of the removable layers of the stack can all be the same; however, some embodiments may include layers that vary in thickness from layer to layer. For example, some layers of the stack can be about 0.008 inches (8 mils) thick, while other layers of the stack can be about 0.002 (2 mils) inches thick. In some embodiments, the thickness of the layers of adhesive may be negligible. By way of example and not limitation, if three (3) 0.001 inch (1 mil) thick layers are stacked upon and adhered to each other, the adhesive layers may be of negligible thickness so that the stack of three layers would still measure about 0.003 inches thick. In some embodiments, the thickness of the adhesive layers can be about 0.00059 inches (i.e., about 0.59 mils, or about 15 microns) thick.

The system disclosed herein has been described in relation to adhering a stack of removable layers to a face shield of a helmet. However, it is also contemplated that the stack can be adhered, for example, to other eye protectors, such as an eye shield of a goggle. In such an example, the eye shield of the goggle may be fabricated from a flexible film layer configured to inhibit, limit, or prevent snow and/or dirt from irritating the user's eyes when skiing during a snowfall, or riding a motocross motorcycle through dirt and/or mud. In this manner, the refractive indices of the removable layers and the adhesive layers of the stack can be matched to the flexible film layer of the goggle so that the refractive indices of the removable layers of the stack, the adhesive layers of the stack, and the flexible film layer of the goggle are all matched within 0.2 of each other.

In some embodiments, stacks can be configured for dry mounting to lenses or shields that already have pins installed thereon. For example, the stack can be provided with holes configured to align with the pins mounted in such lens or shield, while also including the dry mount adhesive layer on the lower surface of the stack. In this manner, consumers will not need to dispose of older eye protectors, face shields, helmets, etc., in order to use the stacks of the present disclosure. Additionally and/or alternatively, stacks can be manufactured in a shape and configuration designed to not interfere with any existing pins or other objects on a lens or shield. In this manner, the stacks can be configured to be used on eye protectors of varying shapes, sizes and configurations, regardless of whether the eye protector is equipped to handle pin mounts.

The above description is given by way of example, and not limitation. Given the above disclosure, one skilled in the art could devise variations that are within the scope and spirit of the invention disclosed herein, including various ways of applying the adhesive to the layers. Further, the various features of the embodiments disclosed herein can be used alone, or in varying combinations with each other and are not intended to be limited to the specific combination described herein. Thus, the scope of the claims is not to be limited by the illustrated embodiments. All references cited in the present disclosure are hereby incorporated by reference in their entirety.

What is claimed is:

1. A method of protecting an eye protector without significantly reducing visual acuity through the eye protector, the eye protector having a center portion defining a center of gaze of a wearer, the eye protector also having a lens configured to protect the wearer from projectiles, the lens having a lens refractive index, the method comprising:
    selecting an optically clear stack having at least one removable layer, each removable layer having a removable layer refractive index matched to within about 0.2 of the lens refractive index;
    removing a protective liner from a bottom surface of the lens stack to expose an optically clear dry mount adhesive layer, and
    dry mounting the stack to the lens so that the adhesive layer forms a continuous and uninterrupted adhesive layer over at least the center portion,
    wherein the dry mount adhesive layer is self-wetting and has a dry mount adhesive layer refractive index matched to within about 0.2 of the lens refractive index and each removable layer refractive index.

2. The method of claim 1, wherein the selecting step comprises selecting a stack having a plurality of removable layers.

3. The method of claim 2, wherein the dry mounting step further comprises the step of removing air between the stack and the lens after the stack is dry mounted to the lens.

4. The method of claim 3, further comprising the step of breaking an adhesive bond between the stack and an uppermost removable layer of the stack to remove the uppermost removable layer, the breaking step further comprising gripping and pulling a tab on the uppermost layer of the stack to remove the uppermost layer and expose a lower layer of the stack, wherein the adhesive bond is formed by an optically clear stack adhesive layer having a stack adhesive refractive index,
    wherein the stack adhesive layer refractive index, the lens refractive index, each removable layer refractive index, and the dry mount adhesive refractive index are matched to within about 0.2.

5. The method of claim 4, wherein the step of dry mounting establishes a peel strength between the stack and the lens that is greater than a peel strength between each removable layer and the stack.

* * * * *